US011202449B2

(12) United States Patent
Belfort et al.

(10) Patent No.: US 11,202,449 B2
(45) Date of Patent: *Dec. 21, 2021

(54) ANTI-MICROBIAL PEPTIDES AND METHOD FOR DESIGNING NOVEL ANTI-MICROBIAL PEPTIDES

(71) Applicants: RENSSELAER POLYTECHNIC INSTITUTE, Troy, NY (US); HEALTH RESEARCH, INC., Menands, NY (US)

(72) Inventors: Georges Belfort, Albany, NY (US); C. Seth Pearson, Albany, NY (US); Brian Murray, Haverhill, MA (US); Pankaj Sakharam Karande, Troy, NY (US); Jun Ha Kwak, Troy, NY (US); Kathleen A. McDonough, Albany, NY (US); Zachary Andrew Kloos, New Haven, CT (US)

(73) Assignees: Rensselaer Polytechnic Institute, Troy, NY (US); Health Research, Inc., Menands, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,652

(22) Filed: May 14, 2019

(65) Prior Publication Data

US 2019/0337984 A1 Nov. 7, 2019

Related U.S. Application Data

(63) Continuation of application No. 15/259,942, filed on Sep. 8, 2016, now Pat. No. 10,336,790, which is a continuation-in-part of application No. PCT/US2015/019761, filed on Mar. 10, 2015.

(60) Provisional application No. 61/950,265, filed on Mar. 10, 2014.

(51) Int. Cl.

| | |
|---|---|
| ***C07K 7/08*** | (2006.01) |
| ***G16B 5/00*** | (2019.01) |
| ***A01N 63/10*** | (2020.01) |
| ***A01N 43/38*** | (2006.01) |
| ***A61K 38/10*** | (2006.01) |
| ***A61K 45/06*** | (2006.01) |
| ***A61K 38/00*** | (2006.01) |
| ***A01N 63/50*** | (2020.01) |

(52) U.S. Cl.

CPC ............. *A01N 63/50* (2020.01); *A01N 43/38* (2013.01); *A61K 38/10* (2013.01); *A61K 45/06* (2013.01); *C07K 7/08* (2013.01); *G16B 5/00* (2019.02); *A61K 38/00* (2013.01)

(58) Field of Classification Search

CPC ........ A01N 43/38; A01N 63/10; A61K 38/00; A61K 38/10; A61K 45/06; C07K 7/08; G16B 5/00

See application file for complete search history.

(56) References Cited

U.S. PATENT DOCUMENTS

| | | | | |
|---|---|---|---|---|
| 6,551,795 B1 * | 4/2003 | Rubenfield | C07K 14/21 | 435/253.3 |
| 7,504,490 B1 | 3/2009 | Weinstock et al. | | |
| 7,754,676 B2 * | 7/2010 | Kwak | A61K 39/00117 | 514/19.3 |
| 7,915,040 B2 * | 3/2011 | Kwak | A61K 31/7088 | 435/325 |
| 8,084,250 B2 * | 12/2011 | Kwak | A61P 31/12 | 435/320.1 |
| 8,252,737 B2 | 8/2012 | Hodges et al. | | |
| 8,551,936 B2 * | 10/2013 | Kwak | A61P 31/18 | 514/1 |
| 8,551,954 B2 | 10/2013 | Schmidtchen et al. | | |
| 8,680,058 B2 | 3/2014 | Eckert et al. | | |
| 8,754,030 B2 * | 6/2014 | Kwak | A61P 31/12 | 514/1 |
| 8,809,262 B2 | 8/2014 | Beuerman et al. | | |
| 10,336,790 B2 * | 7/2019 | Belfort | A01N 43/38 | |
| 10,513,546 B2 * | 12/2019 | Watters | C07K 14/4737 | |
| 2007/0065908 A1 | 3/2007 | Gallo et al. | | |
| 2009/0117093 A1 | 5/2009 | Kim | | |
| 2011/0236429 A1 | 9/2011 | Hancock et al. | | |
| 2014/0142027 A1 | 5/2014 | Beuerman et al. | | |

FOREIGN PATENT DOCUMENTS

| | | |
|---|---|---|
| WO | 2000008168 A2 | 2/2000 |
| WO | 2001081581 A2 | 11/2001 |
| WO | 2013078217 A2 | 5/2013 |

OTHER PUBLICATIONS

Vandekerckhove et al. The Primary Structure of Protein S16 From *Eschericttla coli* Ribosomes. FEBS Letters, vol. 73, No. 1, pp. 18-21. (Year: 1977).*

International Search Report and Written Opinion issued in PCT/US2015/019761, dated Aug. 12, 2015.

Q4WK55, UniProtKB/TrEMBL Accession No. Q4WK55, Dec. 11, 2013 [online], [Retrieved on Aug. 3, 2015], Retrieved from the Internet: URL: http://www.unlprotorg/uniprot/Q4WK55.txt?version=31. Entire document.

B0XN17, UniProtKB/TrEMBL. Accession No. B0XN17, Nov. 13, 2013 [online]. [Retrieved on Aug. 3, 2015]. Retrieved from the internet URL: http://www.uniprot.org/uniprot/B0XN1.txt?version=17. Entire document.

B8MFE7, UniProtKB/TrEMBL. Accession No. B8MFE7, Nov. 13, 2013 [online]. [Retrieved on Aug. 3, 2015]. Retrieved from the internet URL: http://www.uniprot.org/uniprot/B8MFE7.txt?version=20. Entire document.

(Continued)

*Primary Examiner* — Marcela M Cordero Garcia

(74) *Attorney, Agent, or Firm* — Murtha Cullina LLP; Anthony P. Gangemi

(57) ABSTRACT

Disclosed herein are novel anti-microbial peptides with inhibitory activity against *M. tuberculosis* and *streptococcus* bacteria. Additionally, a method for designing novel anti-microbial peptides is disclosed.

14 Claims, 7 Drawing Sheets

Specification includes a Sequence Listing.

(56) References Cited

OTHER PUBLICATIONS

A1D4Q0, UniProtKB/TrEMBL. Accession No. A1D4Q0, Nov. 2013 [online]. [Retrieved on Aug. 3, 2015]. Retrieved from the internet URL: http://www.uniprot.org/uniprot/A1D4Q0.txt?version=32. Entire document.
Zasloff, M., "Antimicrobial Peptides of Multicellular Organisms," Nature, 415:389-395 (2002).
Collins et al., "Microplate Alamar Blue Assay versus BACTEC 460 Systems for High-Throughput Screening of Compounds against Mycobacterium tuberculosis and *Mycobacteriam avium*," Antimicrobial Agents and Chemotherapy, 41 (5): 1004-1009 (1997).
Mishra et al., "Ab Initio Design of Potent Anti-MRSA Peptides Based on Database Filtering Technology," Journal of the American Chemical Society, 134(3): 12426-12429 (2012).
Wimley, William C., "Describing the Mechanism of Antimicrobial Peptide Action with the Interfacial Activity Model," ACS Chemical Biology, 5(10):905-917 (2010).
Parkhill, J., et al., "Complete genome sequence of a multiple drug resistant *Salmonella enterica* serovar Typhi CT18," Nature; London col. 413, No. 6858, pp. 848-852 (2001).

* cited by examiner

ANTI-MICROBIAL PEPTIDES AND METHOD FOR DESIGNING NOVEL ANTI-MICROBIAL PEPTIDES

CROSS-REFERENCE TO RELATED APPLICATIONS

The present application is a continuation of U.S. Non-Provisional patent application Ser. No. 15/259,942, filed Sep. 8, 2016, which is a Continuation-In-Part application of International Application No. PCT/US2015/019761, filed on Mar. 10, 2015, and published as WO 2015/138494 A1 on Sep. 17, 2015, which claims the benefit of U.S. Provisional Patent Application Ser. No. 61/950,265, filed on Mar. 10, 2014. The contents of each of the prior applications are hereby incorporated by reference herein in their entirety.

STATEMENT ON FEDERALLY SPONSORED RESEARCH OR DEVELOPMENT

This invention was made with government support under NIH Grant Numbers R01AI063499 and T32GM067545 awarded by the National Institutes of Health and NSF Grant Number EAGER (CBET 1122780) awarded by the National Science Foundation. The government has certain rights in the invention.

FIELD OF THE INVENTION

This invention relates to anti-microbial peptides with inhibitory activity against *M. tuberculosis* and *streptococcus* bacteria. This invention also relates to a method for designing novel anti-microbial peptides.

BACKGROUND OF THE INVENTION

Antibiotic resistance is increasing at an alarming rate, especially for the drug resistant form of *Mycobacterium tuberculosis* which killed an estimated 170,000 people in 2012 according to the U.S. Centers for Disease Control and Prevention. Alternatives to traditional antibiotics are urgently needed to combat these resistant bacteria. Disrupting bacterial, but not mammalian, outer membrane integrity with peptides is one such strategy to destroy pathogenic bacteria in a highly selective manner. Design strategies to develop potent, stable antimicrobial peptides ("AMPs") are urgently needed.

AMPs are typically short, cationic peptides that usually adopt an alpha helical conformation. Upon discovery of naturally-occurring AMPs, many were tested for activity against *M. tuberculosis* including human and rabbit defensins and porcine protegrins. The most potent of these displayed >90% killing of *M. tuberculosis* at 50 μg/mL and acted by a mechanism which produced visible lesions on the mycobacterial outer membrane. Subsequently, several of the broadly active natural peptides were modified and tested against *M. tuberculosis* with minimum inhibitory concentrations ("MICs") as low as 10 μM. Large, entirely synthetic libraries were also tested against *M. tuberculosis* with MICs reported as low as 1 μM. In addition, peptoids, which are more resistant to degradation than peptides, were developed with MIC values as low as 6 μM.

Despite clear evidence of their efficacy, the mechanism of action of AMPs remains debated, though it is believed that the majority of AMPs act through disruption of microbial membranes. Recently, many insights have been gained into the motifs that govern the effectiveness of short alpha helical AMPs. The three main parameters that guide effectiveness are peptide hydrophobicity, peptide charge and the distribution of charged and hydrophobic residues. Activity is dependent on a mixture of hydrophobic and cationic residues, arranged to form an amphipathic peptide.

It has been proposed that the cationic portion targets the peptide to the negatively charged bacterial membrane, while the hydrophobic portion allows for intercalation into the membrane and subsequent disruption of the membrane via a number of proposed mechanisms. This amphipathic character lends itself to design due to the periodicity of the alpha helical arrangement. Peptides can be visualized in two dimensions using helical wheel diagrams and sequences bearing separate cationic and hydrophobic faces can be designed.

The majority of prior studies have focused on either optimizing naturally-occurring peptides or screening large random synthetic libraries to develop potential drug candidates against a specific microbial target or investigating the general mechanism of action. We have developed a novel method for designing a novel peptide that uses bioinformatics and rational design informed by known mechanistic rules, to develop a set of more potent initial peptides than those found in nature while avoiding the need to screen large randomly constructed libraries. Specifically, we have combined a de novo design approach called Database Filtering with protein engineering, rational design, and three dimensional ("3-D") modeling to design potent AMPs against a selected microbial target. Database Filtering uses a library of peptides with reported activity against the bacterium of choice to determine a characteristic peptide length, overall charge and hydrophobicity, and commonly occurring residues, resulting in a set of amino acids. Our method then employs rational design including the use of helical wheel diagrams to arrange the set of amino acids in a way that maximizes the amphipathic nature of the peptide. 3-D modeling is then employed to verify an alpha-helical conformation and proper distribution of amino acids to generate the amphipathic surface.

We've successfully used our novel method to design novel AMPs which demonstrated high potency against *M. tuberculosis* and other microbes, such as *streptococcus* bacteria.

SUMMARY OF THE INVENTION

The present invention relates to an isolated peptide comprising a sequence $X_1X_2X_3X_4X_5X_6X_7X_8X_9X_{10}X_{11}X_{12}X_{13}$ (SEQ ID NO: 6), wherein $X_1$, $X_2$, $X_4$, $X_6$, and $X_{ii}$ are each a hydrophobic amino acid, wherein $X_3$ is selected from the group consisting of S, T, N, and Q, wherein $X_5$, $X_{12}$, and $X_{13}$ are each a cationic amino acid, wherein $X_7$, $X_8$, $X_9$, and $X_{10}$ are selected from the group consisting of a hydrophobic amino acid and a cationic amino acid, wherein $X_7$ and $X_8$ cannot both be a hydrophobic amino acid and cannot both be a cationic amino acid, and wherein $X_9$ and $X_{10}$ cannot both be a hydrophobic amino acid and cannot both be a cationic amino acid.

In another embodiment, the present invention relates to an isolated peptide comprising a sequence ILSLRW$X_7X_8X_9X_{10}$WKK (SEQ ID NO: 5), wherein $X_7$ and $X_8$ are selected from the group consisting of R and W, wherein $X_7$ and $X_8$ are not the same, and wherein $X_9$ and $X_{10}$ are selected from the group consisting of K and W, wherein $X_9$ and $X_{10}$ are not the same.

In another embodiment, the present invention relates to an isolated peptide comprising a sequence ILSLRWRWKWWKK (SEQ ID NO: 1).

In another embodiment, the present invention relates to an isolated peptide of claim 1 comprising a sequence ILSLRWWRKWWKK (SEQ ID NO: 2).

In another embodiment, the present invention relates to an isolated peptide of claim 1 comprising a sequence ILSLRWRWWKWKK (SEQ ID NO: 3).

In another embodiment, the present invention relates to an isolated peptide comprising a sequence IRKLKSWKWLRWL (SEQ ID NO: 4).

In another embodiment, the present invention relates to nucleic acids encoding the peptides of the invention.

The peptides of the invention, which inhibit *M. tuberculosis* and *streptococcus* bacteria, find utility in the treatment of and prevention of tuberculosis infection, tuberculosis disease, and streptococcal infections.

Accordingly, in another embodiment, the present invention relates to compositions comprising at least one of the disclosed peptides, wherein the composition may include a pharmaceutically acceptable buffer, diluent, carrier, adjuvant, or excipient. These compositions may also include at least one antibiotic agent.

In another embodiment, the present invention relates to a method for treating or preventing a microbial infection in or on a subject in need thereof, the method comprising administering to the subject a therapeutically effective amount of at least one of the disclosed peptides, optionally also administering to the subject at least one antibiotic agent, wherein the antibiotic agent is administered simultaneously or sequentially with the disclosed peptide.

In another embodiment, the present invention relates to a method of disinfecting a surface of an article, the method comprising applying to the surface of the article a composition comprising at least one of the disclosed peptides.

In another embodiment, the present invention relates to a disinfecting solution comprising at least one of the disclosed peptides and an acceptable carrier.

In yet another embodiment, the present invention relates to a method for designing a novel peptide, the method comprising:

(a) identifying a set of anti-microbial peptides having inhibitory activity against a chosen microbe;

(b) determining most common length of the anti-microbial peptides within the set;

(c) determining most common net charge of the anti-microbial peptides within the set;

(d) determining most common range of hydrophobicity of the anti-microbial peptides within the set;

(e) determining most common amino acids of the anti-microbial peptides within the set;

(f) optionally, determining at least one common motif present in the anti-microbial peptides within the set, wherein steps (b) through (e) and the optional step (f) are performed sequentially, non-sequentially, or simultaneously;

(g) designing an amino acid sequence of the novel peptide by selecting amino acids of the novel peptide using a helical wheel diagram, wherein the novel peptide has the most common length determined in step (b), has the most common net charge determined in step (c), has the most common hydrophobicity determined in step (d), consists of the most common amino acids determined in step (e), and, optionally, has the at least one common motif determined in step (f), wherein the novel peptide has one or more hydrophobic faces and one or more hydrophilic faces as predicted by the helical wheel diagram, wherein at least one hydrophobic face of the one or more hydrophobic faces includes at least one hydrophobic face interruption, wherein the at least one hydrophobic face interruption is positioned within the at least one hydrophobic face and consists of one or two amino acids selected from the group consisting of K, R, H, S, T, N, Q, and combinations thereof;

(h) employing a software program to generate a three dimensional model of the novel peptide having the amino acid sequence designed in step (g);

(i) confirming that the three dimensional model of the novel peptide generated in step (h) has an alpha helical structure;

(j) confirming that the three dimensional model of the novel peptide generated in step (h) has the one or more hydrophobic faces and the one or more hydrophilic faces, wherein steps (i) and (j) are performed sequentially, non-sequentially, or simultaneously;

(k) repeating steps (g) through (j) if the three dimensional model generated in step (h) does not have an alpha helical structure, does not have the one or more hydrophobic faces, or does not have the one or more hydrophilic faces.

The method of the invention has utility in designing novel anti-microbial peptides.

DETAILED DESCRIPTION OF THE INVENTION

Figure 1:
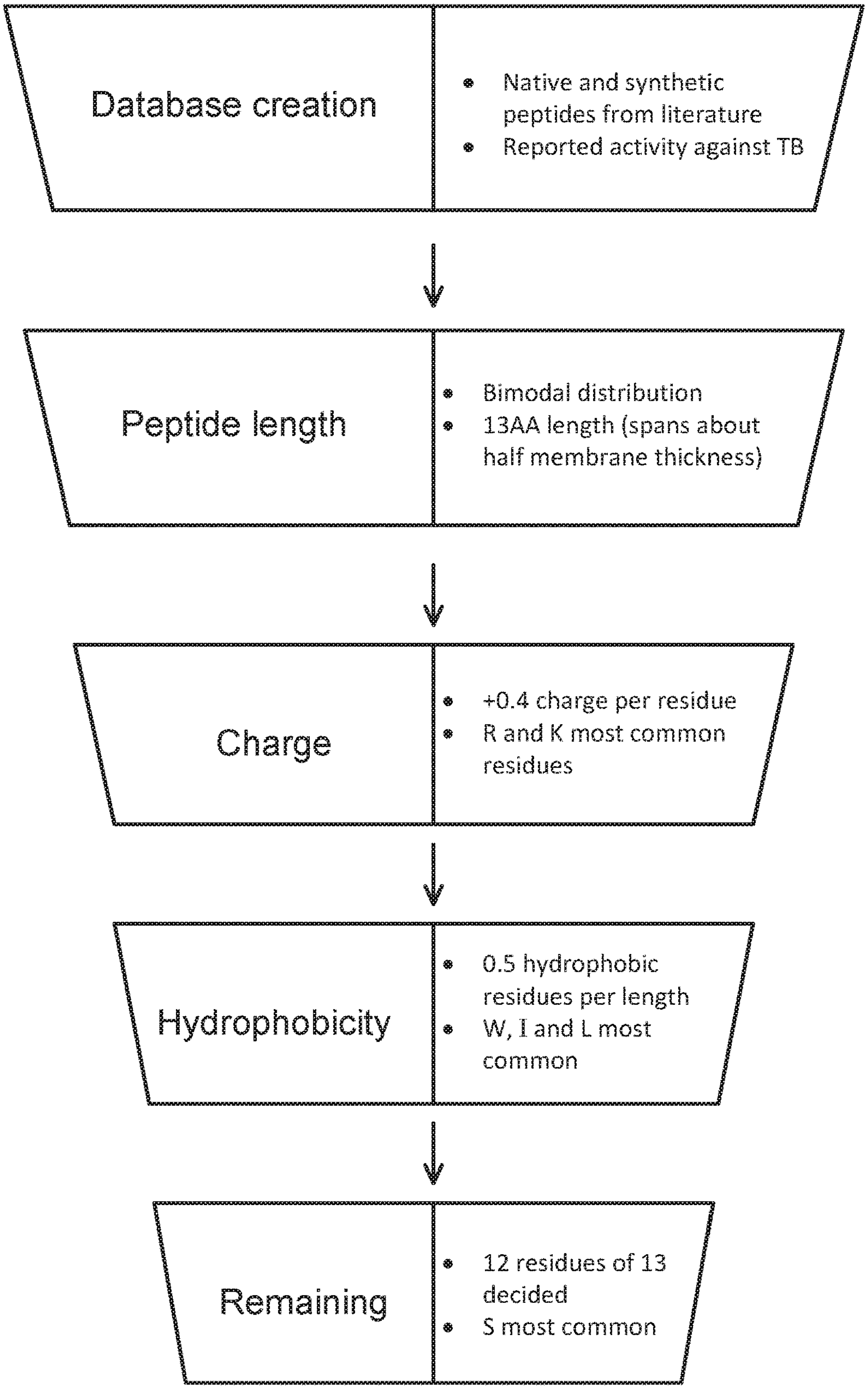
FIG. 1 illustrates an example of the process of database analysis by identifying a set of anti-microbial peptides having inhibitory activity against *M. tuberculosis* ("Database creation" step), determining most common length of the anti-microbial peptides within the set ("Peptide length" step), determining most common net charge of the anti-microbial peptides within the set ("Charge" step), determining most common range of hydrophobicity of the anti-microbial peptides within the set ("Hydrophobicity" step), determining most common amino acids of the anti-microbial peptides within the set (in this example, performed during "Charge," "Hydrophobicity," and "Remaining" steps).

The invention relates to an isolated peptide comprising a sequence $X_1X_2X_3X_4X_5X_6X_7X_8X_9X_{10}X_{11}X_{12}X_{13}$ (SEQ ID NO: 6), wherein $X_1$, $X_2$, $X_4$, $X_6$, and $X_{11}$ are each a hydrophobic amino acid, wherein $X_3$ is selected from the group consisting of S, T, N, and Q, wherein $X_5$, $X_{12}$, and $X_{13}$ are each a cationic amino acid, wherein $X_7$, $X_8$, $X_9$, and $X_{10}$ are selected from the group consisting of a hydrophobic amino acid and a cationic amino acid, wherein $X_7$ and $X_8$ cannot both be a hydrophobic amino acid and cannot both be a cationic amino acid, and wherein $X_9$ and $X_{10}$ cannot both be a hydrophobic amino acid and cannot both be a cationic amino acid.

In one embodiment, $X_7$ and $X_8$ are selected from the group consisting of R and W, wherein $X_7$ and $X_8$ are not the same. In another embodiment, $X_9$ and $X_{10}$ are selected from the group consisting of K and W, wherein $X_9$ and $X_{10}$ are not the same. In another embodiment, $X_1$, $X_2$, $X_4$, $X_6$, and $X_{11}$ are selected from the group consisting of I, L, and W.

In one embodiment, $X_3$ is S or T, and preferably S. In one preferred embodiment, $X_5$, $X_{12}$, and $X_{13}$ are selected from the group consisting of K and R.

The invention also relates to an isolated peptide comprising a sequence ILSLRW$X_7X_8X_9X_{10}$WKK (SEQ ID NO: 5), wherein $X_7$ and $X_8$ are selected from the group consisting of R and W, wherein $X_7$ and $X_8$ are not the same, and wherein $X_9$ and $X_{10}$ are selected from the group consisting of K and W, wherein $X_9$ and $X_{10}$ are not the same.

The invention also relates to an isolated peptide of comprising a sequence ILSLRWRWKWWKK (SEQ ID NO: 1), the isolated peptide comprising a sequence ILSLRWWRKWWKK (SEQ ID NO: 2), the isolated peptide comprising a sequence ILSLRWRWWKWKK (SEQ ID NO: 3), and an isolated peptide comprising a sequence IRKLKSWKWLRWL (SEQ ID NO: 4).

In one embodiment, any peptide of the invention comprises at least one D-amino acid.

Furthermore, the peptides of the invention may have at least one modification selected from modification at the C-terminal part by amidation or esterification and modification at the N-terminal part by acylation, acetylation, myristoylation, PEGylation, alkylation, palmitoylation, and the like. The modification may also be halogenation. The halogenation may typically be a halogenation of a Trp side chain.

Further, any amino acid residue of the peptides of the invention may comprise an amino acid having at least one protecting group. The protecting groups may comprise Boc, But, Fmoc, be or any other protecting group. A protected amino acid is an amino acid with one or more of its reactive groups modified with an inert molecule, to reduce and/or prevent chemical reactions of the reactive group.

In another embodiment, the invention relates to a composition comprising at least one peptide of the invention and a pharmaceutically acceptable buffer, diluent, carrier, adjuvant, or excipient. This composition may further comprise at least one antibiotic agent.

The antibiotic agent may be selected from the group consisting of isoniazid, rifampicin, pyrazinamide, ethambutol, levofloxacin, moxifloxacin, ofloxacin, kanamycin, amikacin, capreomycin, streptomycin, bedaquiline, para-aminoslicyclic acid, cycloserine, penicillin, amoxicillin, azithromycin, clarithromycin, erythromycin, cephalosporin, and combinations thereof.

The invention also relates to a method for treating or preventing a microbial infection in or on a subject in need thereof, the method comprising administering to the subject a therapeutically effective amount of at least one peptide of the invention. This method may further comprise administering to the subject at least one antibiotic agent, wherein the antibiotic agent is administered simultaneously or sequentially with the at least one peptide of the invention. The subject may be a mammal.

The microbial infection may be a tuberculosis infection or a tuberculosis disease. In this case, the co-administered antibiotic agent may be selected from the group consisting of isoniazid, rifampicin, pyrazinamide, ethambutol, levofloxacin, moxifloxacin, ofloxacin, kanamycin, amikacin, capreomycin, streptomycin, bedaquiline, para-aminoslicyclic acid, cycloserine, and combinations thereof.

Additionally, the microbial infection may be a streptococcal infection. In this case, the co-administered antibiotic agent may be selected from the group consisting of penicillin, amoxicillin, azithromycin, clarithromycin, erythromycin, cephalosporin, and combinations thereof.

Streptococcal infection may be strep throat, scarlet fever, impetigo, toxic shock syndrome, cellulitis and necrotizing fasciitis (flesh-eating disease), blood infections, pneumonia and meningitis.

The above methods for treating or preventing a microbial infection may further comprise administering the peptide in the form of a composition comprising the peptide and a pharmaceutically acceptable buffer, diluent, carrier, adjuvant, or excipient.

The invention also relates to a method of disinfecting a surface of an article, the method comprising applying to the surface of the article a composition comprising at least one of the peptides of the invention. Such article may be clothes (e.g., clothes of healthcare workers or military personnel), walls (e.g., walls in hospital rooms), or particles intended for release into the air to kill or reduce pathogens.

The invention also relates to a disinfecting solution comprising at least one peptide of the invention and an acceptable carrier.

The invention also relates to a method for designing a novel peptide, the method comprising: (a) identifying a set of anti-microbial peptides having inhibitory activity against a chosen microbe; (b) determining most common length of the anti-microbial peptides within the set; (c) determining most common net charge of the anti-microbial peptides within the set; (d) determining most common range of hydrophobicity of the anti-microbial peptides within the set; (e) determining most common amino acids of the anti-microbial peptides within the set, (f) optionally, determining at least one common motif present in the anti-microbial peptides within the set, wherein steps (b) through (e) and the optional step (f) are performed sequentially, non-sequentially, or simultaneously; (g) designing an amino acid sequence of the novel peptide by selecting amino acids of the novel peptide using a helical wheel diagram, wherein the novel peptide has the most common length determined in step (b), has the most common net charge determined in step (c), has the most common hydrophobicity determined in step (d), consists of the most common amino acids determined in step (e), and, optionally, has the at least one common motif determined in step (f), wherein the novel peptide has one or more hydrophobic faces and one or more hydrophilic faces as predicted by the helical wheel diagram, wherein at least one hydrophobic face of the one or more hydrophobic faces includes at least one hydrophobic face interruption, wherein the at least one hydrophobic face interruption is positioned within the at least one hydrophobic face and consists of one or two amino acids selected from the group consisting of K, R, H, S, T, N, Q, and combinations thereof, (h) employing a software program to generate a three dimensional model of the novel peptide having the amino acid sequence designed in step (g); (i) confirming that the three dimensional model of the novel peptide generated in step (h) has an alpha helical structure; (j) confirming that the three dimensional model of the novel peptide generated in step (h) has the one or more hydrophobic faces and the one or more hydrophilic faces, wherein steps (i) and (j) are performed sequentially, non-sequentially, or simultaneously; (k) repeating steps (g) through (j) if the three dimensional model generated in step (h) does not have an alpha helical structure, does not have the one or more hydrophobic faces, or does not have the one or more hydrophilic faces.

In this method for designing the novel peptide, the amino acid sequence of the novel peptide may have a cationic amino acid at least one terminus.

The invention also relates to the above method for designing the novel peptide, further comprising synthesizing the novel peptide. This method may further comprise testing the novel peptide for anti-microbial properties.

The antimicrobial peptides may be synthesized by standard chemical methods, including synthesis by automated procedure. In general, peptide analogues are synthesized based on the standard solid-phase Fmoc protection strategy with HATU (N-[DIMETHYLAMINO-1H-1.2.3.-TRIAZOLO[4,5-B]PYRIDIN-1-YLMETHYLELE]-N-METHY-LMETHANAMINIUM HEXAFLUOROPHOSPHATE N-OXIDE) as the coupling agent or other coupling agents such as HOAt-1-HYDROXY-7-AZABENZOTRIAZOLE. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides.

Peptides may alternatively be synthesized by recombinant production (see e.g., U.S. Pat. No. 5,593,866). A variety of host systems are suitable for production of the peptide analogues, including bacteria, such as *E. coli*, yeast, such as *Saccharomyces cerevisiae* or *pichia*, insects, such as Sf9, and mammalian cells, such as CHO or COS-7. There are many expression vectors available to be used for each of the hosts and the invention is not limited to any of them as long as the vector and host is able to produce the antimicrobial peptide. Vectors and procedures for cloning and expression in *E. coli* can be found in for example Sambrook et al. (Molecular Cloning: A Laboratory Manual, Cold Spring Harbor Laboratory Press, Cold Spring Harbor, N.Y., 1987) and Ausubel et al. (Current Protocols in Molecular Biology, Greene Publishing Co., 1995).

In one preferred embodiment, the most common length of the anti-microbial peptides within the set is 11, 12, 13, 14, or 15, preferably 13, amino acids. In another preferred embodiment, the most common length of the anti-microbial peptides within the set is 24, 25, 26, 27, or 28, preferably 26 amino acids.

In general the terms and phrases used herein have their art-recognized meaning, which can be found by reference to standard texts, journal references and contexts known to those skilled in the art. The following definitions are provided to clarify their specific use in the context of the invention.

When used herein, the term "amino acid" is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g., diamino butyric acid and diamino propionic acid and the like. Naturally occurring alpha amino acids are preferred.

The following amino acid name abbreviations are used herein: A or Ala for Alanine; M or Met for Methionine; C or Cys for Cysteine; D or Asp for Aspartic Acid; E or Glu for Glutamic Acid; F or Phe for Phenylalanine; G or Gly for Glycine; H or His for Histidine; I or Ile for Isoleucine; K or Lys for Lysine; L or Leu for Leucine; N or Asn for Asparagine; P or Pro for Proline; Q or Glu for Glutamine; R or Arg for Arginine; S or Ser for Serine; T or Thr for Threonine; V or Val for Valine; W or Trp for Tryptophan; and Y or Tyr for Tyrosine.

The antimicrobial peptides of the invention are composed of amino acids linked together by peptide bonds. The peptides are in general in alpha helical conformation under hydrophobic conditions. Sequences are conventionally given from the amino terminus to the carboxyl terminus. Unless otherwise noted, the amino acids are L-amino acids.

When all the amino acids are of L-configuration, the peptide is said to be an L-enantiomer. When all the amino acids are of D-configuration, the peptide is said to be a D-enantiomer.

The term "minimum inhibitory concentration" (MIC) refers to the lowest concentration of an antimicrobial agent (e.g., a peptide) required to prevent growth or otherwise modify a function of a microorganism under certain conditions, for example in liquid broth medium, and can be determined for a number of different microorganisms according to standard techniques well known in the art.

The term "antimicrobial activity" refers to the ability of a peptide of the present invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of an inventive peptide to kill at least one bacterial species. In a particular embodiment, the bacterial species is selected from the group consisting of gram-positive and gram-negative bacteria. In an embodiment, the term can be manifested as microbicidal or microbistatic inhibition of microbial growth.

The term "microorganism" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed. Bacteria can include gram-negative and gram-positive bacteria in addition to organisms classified in orders of the class Mollicutes and the like, such as species of the *Mycoplasma and* Acholeplasma genera. Specific examples of potentially sensitive gram-negative bacteria include, but are not limited to, yi Escherichia coli, Pseudomonas aeruginosa, Salmonella, Hemophilus influenza, Neisseria, Vibrio cholerae, Vibrio parahaemolyticus and *Helicobacter pylori*. Examples of potentially sensitive gram-positive bacteria include, but are not limited to, *Staphylococcus aureus, Staphylococcus epidermis, Streptococcus agalactiae*, Group A *streptococcus, Streptococcus pyogenes, Enterococcus faecalis*, Group B gram positive *streptococcus, Corynebacterium xerosis*, and *Listeria monocytogenes*. Examples of potentially sensitive fungi include yeasts such as *Candida albicans*. Examples of potentially sensitive viruses include measles virus, herpes simplex virus (HSV-1 and -2), herpes family members (HIV, hepatitis C, vesicular, stomatitis virus (VSV), visna virus, and cytomegalovirus (CMV). Examples of potentially sensitive protozoa include *Giardia.*

The term "hydrophobic amino acid" has a meaning of Tryptophan (W) and any amino acid more hydrophobic than Threonine (T) on the hydrophobicity scale of Kyte and Doolittle (Kyte and Doolittle, J. Mol. Biol., 157(1):105-132 (1982)). Such hydrophobic amino acids include A, V, I, L, W, F, M, G, and C.

The term "cationic amino acid" is intended to mean an amino acid which has a net positive charge within the pH range of from about 4 to about 12. Cationic amino acids include amino acids K, R, and H.

The term "polar amino acid" includes amino acids S, T, N, and Q.

The term "hydrophilic amino acid" includes any amino acid from the previously defines set of cationic and polar amino acids. Such hydrophilic amino acids include amino acids K, R, H, S, T, N, and Q.

The term "amphipathic" is intended to mean the distribution of hydrophilic and hydrophobic amino acid residues along opposing faces of an alpha helix structure, beta strand, linear, circular, or other secondary conformation, which results in one face of the molecule being predominantly hydrophilic and/or charged and the other face being predominantly hydrophobic. The degree of amphipathicity of a peptide can be assessed by plotting the sequence of amino acid residues by various web-based algorithms, e.g., those found on us.expasy.org/cgi-bin/protscale.pl. The distribution of hydrophobic residues can be visualized by helical wheel diagrams. Secondary structure prediction algorithms, such as GORIV can be found at www.expasy.com.

The step of determining most common length of the anti-microbial peptides within the set involves calculating average of all peptide lengths in the database, wherein the peptides in the database are known to have inhibitory activity against a chosen microbe. The process of determining most common length of the anti-microbial peptide also involves plotting the peptide lengths to look for features such as a bimodal distribution. In the case of a bimodal distribution, the average of a single mode may be selected with a preference for the mode of shorter length.

The step of determining most common net charge of the anti-microbial peptides within the set involves calculating the charge of each peptide in the database, then dividing it by the peptide length. These charges are plotted to assess distribution and then averaged to determine a most common charge per unit length for the set.

The step of determining most common range of hydrophobicity of the anti-microbial peptides within the set involves calculating the number of hydrophobic residues in each peptide in the database and then dividing this number by the peptide length. This number is plotted to assess distribution and then averaged to determine a most number of hydrophobic residues per unit length for the set.

The step of determining most common amino acids of the anti-microbial peptides within the set involves calculating the total number of times each amino acid appears in the database. These amino acids are arranged into three categories: hydrophobic, cationic, and all other. The amino acids with the highest numbers of appearance in each category are considered to be the most common for that category.

The step of determining at least one common motif present in the anti-microbial peptides within the set involves identifying a commonly appearing sequence fragment or identifying a commonly appearing location of a hydrophobic, cationic, or other amino acid(s) in the peptides within the set. For example, we looked at the percentage of peptides in the database that contained a cationic residue at one terminus and a hydrophobic residue at the other terminus compared to peptides with a hydrophobic residue at both termini or a cationic residue at both termini.

The term "helical wheel diagram" means any type of plot or visual representation used to illustrate the properties of alpha helices in proteins and peptides. Typically, the sequence of amino acids that make up a helical region of the protein's secondary structure are plotted in a rotating manner where the angle of rotation between consecutive amino acids is 100.degree., so that the final representation looks down the helical axis.

The term "hydrophobic face" means an area of the peptide surface that contains three or more hydrophobic residues in direct proximity. Proximity is determined by being within one or two positions of each other on a helical wheel diagram, where the entire set of hydrophobic amino acids can be interrupted by no more than two cationic or polar amino acids. Such interruption is referred to here as a hydrophobic face interruption.

The term "hydrophilic face" means an area of the peptide surface that contains three or more cationic amino acids in direct proximity. Proximity is determined by being within one or two positions of each other on a helical wheel diagram, where the entire set of cationic amino acids can be interrupted by no more than two hydrophobic or polar residues. Such interruption is referred to here as a hydrophilic face interruption.

The terms "methods of treating or preventing" mean amelioration, prevention or relief from the symptoms and/or effects associated with a microbial infection. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a subject is intended to include prophylaxis.

The term "isolated" is not meant to exclude artificial or synthetic mixtures with other compounds or materials, or the presence of impurities that do not interfere with the fundamental activity, and that may be present, for example, due to incomplete purification, or the addition of stabilizers.

The peptides of the invention may be substantially pure. The term "substantially pure" refers to a preparation comprising at least 50-60% by weight of the peptide. More preferably, the preparation comprises at least 75% by weight, and most preferably 90-95% or more by weight of the peptide. Purity is measured by the appropriate methods (e.g., mass spectroscopy, reverse phase-high pressure liquid chromatography, and the like).

Additionally the peptides of the invention may be operably linked to other known antimicrobial peptides or other substances, such other peptides, proteins, oligosaccharides, polysaccharides, other organic compounds, or inorganic substances. For example the antimicrobial peptides may be coupled to a substance which protect the antimicrobial peptides from being degraded within a mammal prior to the antimicrobial peptides has inhibited, prevented or destroyed the life of the microorganism.

In an embodiment of the invention, in vitro antimicrobial activity of these peptides demonstrated herein is an accurate predictor of in vivo antimicrobial activity.

Pharmaceutical compositions contain a therapeutically effective amount of one or more of the antimicrobial peptides and a suitable carrier. A therapeutically effective amount of an antimicrobial peptide can be readily determined according to methods well known in the art. For example, the amount will vary depending on the severity of an infection, subject parameters such as the age and the size/weight of a subject with an actual or potential infection of a given microorganism, and the route of administration and the like.

The present invention relates to compositions comprising one or more antimicrobial peptides of the invention in a microbicidal effective amount and a pharmaceutically acceptable carrier. Such compositions may additionally comprise a detergent. The addition of a detergent to such peptide compositions is useful to enhance antibacterial characteristics of the peptides. Although any suitable detergent may be used, the presently preferred detergent is a nonionic detergent such as Tween 20 or 1% NP40. Such antimicrobial pharmaceutical compositions can be formulated and administered in ways, as understood in the art for use local or systemic injection, for oral or topical application. In an embodiment, the antimicrobial peptides of the present invention can comprise from 0.0001% to 50% by weight of such compositions.

It will be understood that a composition for application, e.g., by systemic injection, will contain an antimicrobial peptide in a therapeutically effective amount or a therapeutically effective amount of an antimicrobial peptide can be conjugated to another molecule with specificity for the target cell type. The other molecule can be an antibody, ligand, receptor, or other recognition molecule. In an embodiment, the choice of the peptide is made with consideration of immunogenicity and toxicity for an actually or potentially infected host, effective dose of the peptide, and the sensitivity of the target microbe to the peptide, as known in the art.

In an embodiment, the method of inhibiting the growth of bacteria using the peptides of the invention may further include the addition of one or more other antimicrobial agents (e.g., a conventional antibiotic) for combination or synergistic therapy. The appropriate amount of the peptide administered will typically depend on the susceptibility of a bacterium such as whether the bacterium is Gram negative or Gram positive, and will be easily discernable by one of ordinary skill in the art.

In an embodiment the invention also provides a composition that comprises the peptide, in an amount effective to kill a microorganism, and a suitable carrier. Such compositions may be used in numerous ways to combat microorganisms, for example in household or laboratory antimicrobial formulations using carriers well known in the art.

Where the peptides are to be used as antimicrobial agents, they can be formulated, for example, in buffered aqueous media containing a variety of salts and buffers. Examples of the salts include, but are not limited to, halides, phosphates and sulfates, e.g., sodium chloride, potassium chloride or sodium sulfate. Various buffers may be used, such as citrate, phosphate, HEPES, Tris or the like to the extent that such buffers are physiologically acceptable to the host that is being treated.

Various excipients or other additives may be used, where the peptides are formulated as lyophilized powders, for subsequent use in solution. The excipients may include various polyols, inert powders or other extenders.

"Therapeutically effective" as used herein, refers to an amount of formulation, composition, or reagent, optionally in a pharmaceutically acceptable carrier, that is of sufficient quantity to ameliorate the state of the subject, such as human patient or animal, so treated. "Ameliorate" refers to a lessening of the detrimental effect of the disease state or disorder in the recipient of the therapy. In an embodiment, a peptide of the invention is administered to a subject in need of treatment.

Pharmaceutically acceptable carrier preparations for administration include sterile or aqueous or nonaqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solutions, Ringer's dextrose, dextrose and sodium chloride, lactated Ringer's, or fixed oils. Active therapeutic ingredients are often mixed with excipients that are pharmaceutically acceptable and compatible with the active ingredients. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antioxidants, chelating agents, and inert gases and the like. The actual dosage of the peptides, formulations or compositions containing such peptides can depend on many factors, including the size/weight, age, and health of an organism, however, one of ordinary skill in the art can use the following teachings and others known in the art describing the methods and techniques for determining clinical dosages (Spiker B., Guide to Clinical Studies and Developing Protocols, Raven Press, Ltd., New York, 1984, pp. 7-13, 54-60; Spiker B., Guide to Clinical Trials, Raven Press, Ltd., New York 1991, pp. 93-101; C. Craig. and R. Stitzel, eds., Modern Pharmacology, 2d ed., Little, Brown and Co., Boston, 1986, pp. 127-133; T. Speight, ed., Avery's Drug Treatment: Principles and Practice of Clinical Pharmacology and Therapeutics, 3d ed., Williams and Wilkins, Baltimore, 1987, pp. 50-56; R. Tallarida, R. Raffa and P. McGonigle, Principles in General Pharmacology, Springer-Verlag, new York, 1988, pp. 18-20) to determine the appropriate dosage to use.

In an embodiment, the following dosages are used: generally in the range of about 0.001 mg/kg to about 100 mg/kg and preferably from about 0.001 mg/kg to about 1 mg/kg final concentration are administered per day to an adult in any pharmaceutically acceptable carrier.

In another embodiment, the present invention may be used as a food preservative or in treating food products to control, reduce, or eliminate potential pathogens or contaminants. A peptide of the invention may be used as a disinfectant, for use in or with any product that must remain microbial free or be within certain tolerances. In an embodiment, treatment with a peptide provides at least partial regulation of infection or contamination.

In an embodiment it is also possible to incorporate or distribute the peptides within materials, on devices, or on objects (e.g., on an accessible surface), where microbial growth or viable presence is undesirable, as a method of microbicidal or microbistatic inhibition of microbial growth by administering to the devices or objects a microbicidal or microbistatic effective amount of peptide. In an embodiment, such devices or objects include, but are not limited to, linens, cloth, plastics, latex fabrics, natural rubbers, implantable devices, surfaces, or storage containers.

In an embodiment, the invention provides a method of disinfecting a surface of an article, said method comprising the step of applying to said surface an effective amount of a composition comprising at least one peptide of the invention. In an embodiment, the invention provides a disinfecting solution comprising at least one peptide of the invention and optionally an acceptable carrier.

Throughout this application, various references are referred to. The disclosures of these publications in their entireties are hereby incorporated by reference as if written herein.

The term "mammal" is used in its dictionary sense. Humans are included in the group of mammals, and humans would be the preferred subjects.

Additionally the invention relates to antimicrobial/pharmaceutical compositions comprising at least one peptide of the invention and a pharmaceutical acceptable buffer, diluent, carrier, adjuvant or excipient. Additional compounds may be included in the compositions. These include, for example, chelating agents such as EDTA, EGTA or glutathione. The antimicrobial/pharmaceutical compositions may be prepared in a manner known in the art that is sufficiently storage stable and suitable for administration to humans and animals. The pharmaceutical compositions may be lyophilized, e.g., through freeze drying, spray drying or spray cooling.

"Pharmaceutically acceptable" means a non-toxic material that does not interfere with the effectiveness of the biological activity of the active ingredients, i.e., the peptide(s) of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, IVIES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO, TES, tricine.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the peptide. The adjuvant may be one or more of zinc, copper or silver salts with different anions, for example, but not limited to fluoride, chloride, bromide, iodide, tiocyanate, sulfite, hydroxide, phosphate, carbonate, lactate, glycholate, citrate, borate, tartrate, and acetates of different acyl composition.

The excipient may be one or more of carbohydrates, polymers, lipids and minerals. Examples of carbohydrates include lactose, sucrose, mannitol, and cyclodextrines, which are added to the composition, e.g., for facilitating lyophilization. Examples of polymers are starch, cellulose ethers, cellulose carboxymethylcellulose, alginates, carageenans, hyaluronic acid, polyacrylic acid, polysulphonate, polyethylenglycol/polyethylene oxide, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The characteristics of the carrier are dependent on the route of administration. One route of administration is topical administration. For example, for topical administrations, a preferred carrier is an emulsified cream comprising the active peptide, but other common carriers such as certain petrolatum/mineral-based and vegetable-based ointments can be used, as well as polymer gels, liquid crystalline phases and microemulsions.

The antimicrobial/pharmaceutical compositions may comprise one or more peptides, such as 1, 2, 3 or 4 different peptides in the antimicrobial/pharmaceutical compositions. By using a combination of different peptides the antimicrobial effect may be increased as well as decrease of the possibility that the microorganism to combat might be resistant and/or tolerant against the antimicrobial agent.

Histidin rich and/or kininogen based peptides, particularly as short peptides have limited antimicrobial activity. However if these peptides are in a composition comprising a salt and/or a pH from about 5.0 to about 7.0, the peptides become active, i.e., an enhanced effect is obtained by the addition of a salt and/or a choice of a specific pH range.

The peptide as a salt may be an acid adduct with inorganic acids, such as hydrochloric acid, sulfuric acid, nitric acid, hydrobromic acid, phosphoric acid, perchloric acid, thiocyanic acid, boric acid etc. or with organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid etc. Inorganic salts such as monovalent sodium, potassium or divalent zinc, magnesium, copper calcium, all with a corresponding anion, may be added to improve the biological activity of the antimicrobial composition. An antimicrobial H-rich peptides based on kininogen and histidine-rich glycoprotein may be used in defined solutions, such as gel, where the pH is defined and controlled (e.g., pH 5.5-6.0) to enhance the effects of the added antimicrobial peptides. For example a gel, ointment or bandage, with a defined pH from about 5.0 to about 7.0, such as from about 5.5 to about 6.0 with or without an ionic environment will enhance, control, and localise the function of the antimicrobial peptides.

The antimicrobial/pharmaceutical compositions of the invention may also be in the form of a liposome in which the peptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Preparation of such liposomal formulations is can be found in for example U.S. Pat. No. 4,235,871.

The antimicrobial/pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(carprolactone) (PCL), and polyanhydrides have been widely used as biodegradable polymers in the production of microspheres. Preparations of such microspheres can be found in U.S. Pat. No. 5,851,451 and in EP0213303.

Alternatively, the antimicrobial peptides may be dissolved in saline, water, polyethylene glycol, propylene glycol, ethanol or oils (such as safflower oil, corn oil, peanut oil, cottonseed oil or sesame oil), tragacanth gum, and/or various buffers. The pharmaceutical composition may also include ions and a defined pH for potentiation of action of antimicrobial peptides.

The antimicrobial/pharmaceutical compositions may be subjected to conventional pharmaceutical operations such as sterilisation and/or may contain conventional adjuvants such as preservatives, stabilisers, wetting agents, emulsifiers, buffers, fillers, etc., e.g., as disclosed elsewhere herein.

The antimicrobial/pharmaceutical compositions according to the invention may be administered locally or systemically. Routes of administration include topical, ocular, nasal, pulmonar, buccal, parenteral (intravenous, subcutaneous, and intramuscular), oral, parenteral, vaginal and rectal. Also administration from implants is possible. Suitable antimicrobial preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems characterized by long-range order but short-range disorder (examples include lamellar, hexagonal and cubic phases, either water- or oil continuous), or their dispersed counterparts, gels, ointments, dispersions, suspensions, creams, aerosols, droples or injectable solution in ampule form and also preparations with protracted release of active compounds, in whose preparation excipients, diluents, adjuvants or carriers are customarily used as described above. The pharmaceutical composition may also be provided in bandages or plasters or the like.

The pharmaceutical compositions will be administered to a patient in a pharmaceutically effective dose. By "pharmaceutically effective dose" is meant a dose that is sufficient to produce the desired effects in relation to the condition for which it is administered. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals The pharmaceutical compositions of the invention may be administered alone or in combination with other therapeutic agents, such as antibiotic or antiseptic agents such as antibacterial agents, anti-fuingicides, anti-viral agents, and antiparasitic agents. Examples are penicillins, cephalosporins, carbacephems, cephamycins, carbapenems, monobactams, aminoglycosides, glycopeptides, quinolones, tetracyclines, macrolides, and fluoroquinolones. Antiseptic agents include iodine, silver, copper, clorhexidine, polyhexanide and other biguanides, chitosan, acetic acid, and hydrogen peroxide. These agents may be incorporated as part of the same pharmaceutical composition or may be administered separately.

The present invention concerns both humans and other mammal such as horses, dogs, cats, cows, pigs, camels, among others. Thus the methods are applicable to both human therapy and veterinary applications. The objects, suitable for such treatment may be identified by well-established hallmarks of an infection, such as fever, puls, culture of organisms, and the like. Infections that may be treated with the antimicrobial peptides include those caused by or due to microorganisms. Examples of microorganisms include bacteria (e.g., Gram-positive, Gram-negative), fungi, (e.g., yeast and molds), parasites (e.g., protozoans, nematodes, cestodes and trematodes), viruses, and prions. Specific organisms in these classes are well known (see for example, Davis et al., Microbiology, 3.sup.rd edition, Harper & Row, 1980). Infections include, but are not limited to, chronic skin ulcers, infected acute wounds and burn wounds, infected skin eczema, impetigo, atopic dermatitis, acne, external otitis, vaginal infections, seborrhoic dermatitis, oral infections and parodontitis, candidal intertrigo, conjunctivitis and other eye infections, and pneumonia.

The antimicrobial/pharmaceutical compositions may also be used to in cleansing solutions, such as lens disinfectants and storage solutions or used to prevent bacterial infection in association with urinary catheter use or use of central venous catheters.

Additionally the antimicrobial compositions may be used for prevention of infection post-surgery in plasters, adhesives, sutures, or be incorporated in wound dressings.

The antimicrobial peptides may also be used in polymers, textiles or the like to create antibacterial surfaces or Cosmetics, and personal care products (soap, shampoos, tooth paste, anti-acne, suncreams, tampons, diapers, etc) may be supplemented with the antimicrobial/pharmaceutical compositions.

The following specific non-limiting examples are illustrative of the invention.

Example 1

Bioinformatics and Design

Antimicrobial peptides were designed against *M. tuberculosis*. The design was based on a published database filtering method (Mishra and Wang, J. Am. Chem. Soc., 134(30):12426-12429 (2012)), a method which outputs the most common peptide length and amino acid composition based on a library of natural and synthetic peptides. It is assumed that if this library is selected to include peptides with high potency against a pathogen of choice, the resulting composition will also have antimicrobial activity. We designed our novel peptides by ordering the resulting amino acids using additional bioinformatic techniques, and using a structurally informed approach. A database was created using natural peptides from databanks (APD2, CAMP) and both natural and synthetic peptides reported in the literature (Ramon-Garcia, et al., Antimicrob. Agents Chemother., 57(5):2295-2303 (2013), Linde, et al., J. Antimicrob. Chemother., 47(5):575-580 (2001), Miyakawa, et al., Infect. Immun., 64(3):926-932 (1996), Jiang, et al., Protein Peptide Letters, 18(3): 241-252 (2011)) that have measured activity against *M. tuberculosis*. The database was then analyzed to determine average peptide length, number of hydrophobic residues, number of hydrophilic residues per length, and the most represented residues of each type (FIG. 1), resulting in a defined length and amino acid composition.

Figure 2:
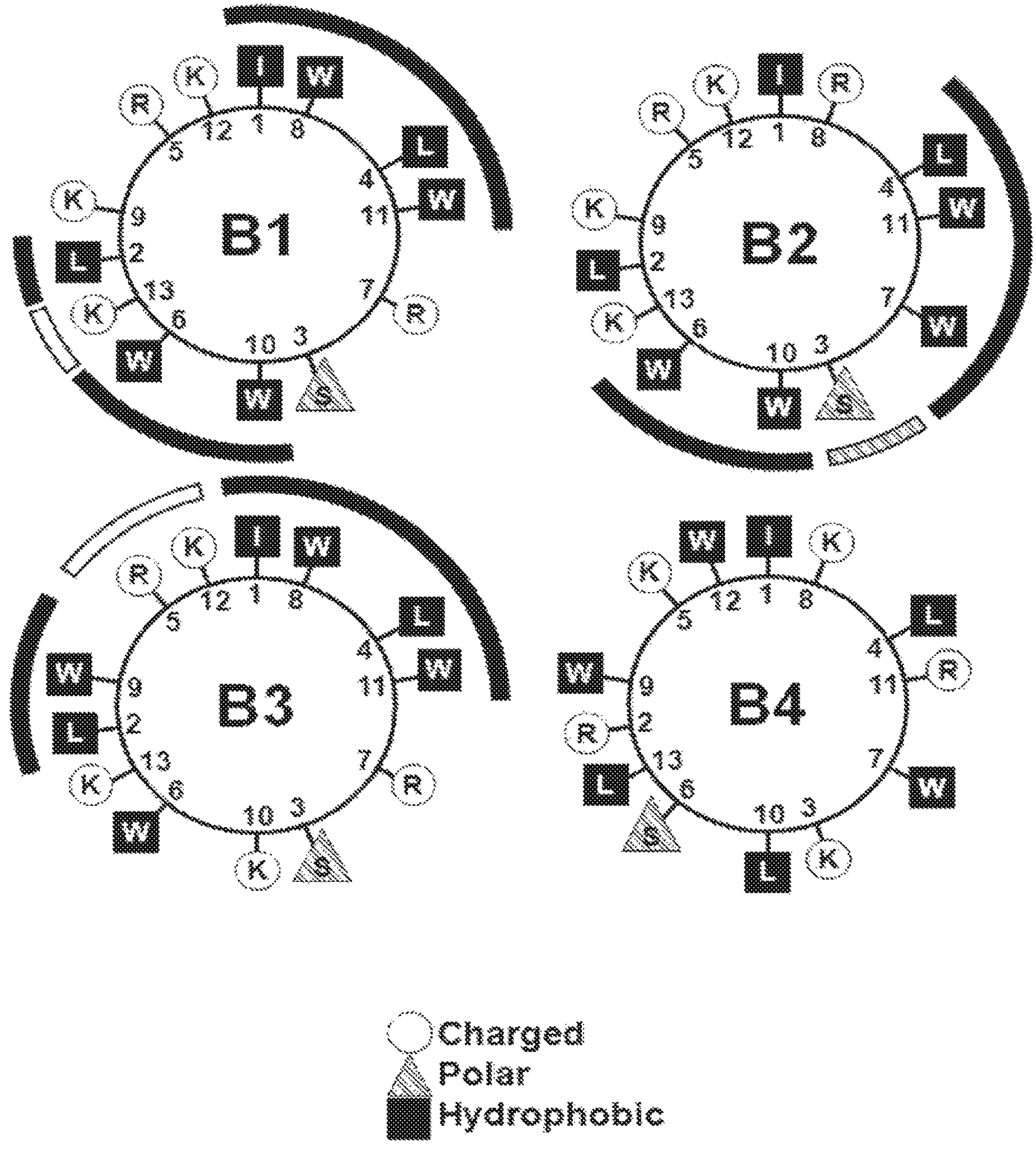
FIG. 2 illustrates use of a helical wheel diagram in designing an amino acid sequence of peptides B1 through B4. Charged (i.e., cationic) amino acids are depicted using white circles, polar amino acid S is depicted using a shaded triangle, and hydrophobic amino acids are depicted using black squares. The helical wheel diagrams demonstrate amphipathic nature of peptides B1 through B3. Specifically, the helical wheel diagram of peptide B1 shows: (a) a hydrophobic face made up of amino acids I1, W8, L4, and W11; (b) a second hydrophobic face made up of amino acids L2, W6, and W10 with a hydrophobic face interruption by amino acid K13; and (c) a hydrophilic face made up of amino acids K9, R5, and K12 (the number after amino acid letter designates the position of that amino acid). The helical wheel diagram of peptide B2 shows: (a) a hydrophobic face made up of amino acids L4, W11, W7, W10, and W6 with a hydrophobic face interruption by amino acid S3; and (b) a hydrophilic face made up of amino acids K13, K9, R5, K12, and R8 with interruptions by hydrophobic amino acids L2 and I1. The helical wheel diagram of peptide B3 shows: (a) a hydrophobic face made up of amino acids L2, W9, I1, W8, L4, and W11, with a hydrophobic face interruption by amino acids R5 and K12; and (b) a hydrophilic face made up of amino acids R7, S3, K10, and K13 with an interruption by a hydrophobic amino acid W6.

Diverging from the database filtering method, which uses bioinformatic-derived sequence motifs for amino acid order, we designed peptides by fitting this set of residues to an alpha helical template (helical wheel diagram) to produce several amphipathic peptides (FIG. 2). The actual conformation for each designed peptide was predicted using PepFold (Thevenet, Shen, et al., Nucleic Acids Res. 40 (Web Server issue):W288-293 (2012)) and the three-dimensional structure of peptides were modeled using the software Molecular Operating Environment ("MOE," Chemical Computing Group, Montreal, Canada).

Results

A database of 44 peptides was generated from databank and literature sources and analyzed using the database filtering method described above. The database contained both natural, broadly active AMPs and synthetic AMPs screened specifically against tuberculosis, providing a breadth of coverage. The average length of the peptides was found to be 13 amino acids and this length was chosen for our designed peptide. The database showed a distinctly bimodal distribution with a group around 12 amino acids (mostly the synthetic peptides) and another group around 26 amino acids (mostly the natural peptides). Interestingly, these values correspond to the approximate length of 13 amino acids of an alpha helical peptide needed to span half a bacterial membrane and to the approximate length of 26 amino acid needed to span an entire bacterial membrane. This observation provides an indication that spanning half the membrane may be sufficient for disruption.

The second parameter analyzed was average charge, which was determined to be +5. All peptides in the database were cationic. When normalized to the length of the peptide, the average charge per amino acid was found to 0.4, a value that was highly consistent across all peptides in the database. Applying this ratio to our novel peptides of 13 amino acids implied that 5 of the residues had to be positively charged.

The average number of hydrophobic residues (A, V, I, L, W, F, M, C) was determined to be 6.5 for the selected peptides. Normalization to the length of each peptide resulted in an average value of 0.5 hydrophobic residues per number of total residues. Applying this value to our peptide of length 13 amino acids suggested a total of 6.5 hydrophobic residues, which was rounded to 7.

Twelve of the thirteen residues were determined to be charged or hydrophobic, leaving one uncharged, non-hydrophobic residue. Thus, we determined that our peptide should contain 5 cationic (K, R, or H), 7 hydrophobic residues (A, V, I, L, W, F, M, G, or C), and 1 uncharged, non-hydrophobic residue (S, T, Y, P, N, or Q).

To select the identity of the cationic residues, the frequency of each residue in the database was analyzed. All peptides in the database contained K, R, or a combination of the two. In contrast, only three peptides in the entire database were found to contain H, so this residue was eliminated. For peptides containing R or K, 20% contained only R, 14% contained only K, and 66% contained both. As a result a mixture of K and R was selected, and of our five cationic residues, three were selected to be K and two were selected to be R.

A similar procedure was followed for hydrophobic residues. A, M, G, and C residues appeared infrequently and were not considered for this reason. Of the remaining five possible hydrophobic residues, W and L appeared most frequently, especially among the subset of peptides approximately 13 amino acids in length. I was also relatively frequent. Thus, four of the seven hydrophobic residues were selected to be W, two of the seven were selected to be L, and one of the seven was selected to be I.

Of the polar residues T, Y, N, and Q appeared infrequently. S appeared more frequently than P and S also better supports an alpha helical conformation. Thus, the final residue was selected to be S.

The overall output of database filtering against tuberculosis resulted in a peptide length of 13 amino acids, containing two R, three K, four Trp, two L, one I, and one S amino acid. Peptide sequences were determined by arranging the selected above set of amino acids in an amphipathic manner on a helical wheel diagram. This arrangement was additionally constrained to have a cationic residue at one terminus, a common motif observation from the database. In total, we developed three novel candidate peptides having the following sequences:

```
Peptide B1 sequence:
                                    (SEQ ID NO: 1)
ILSLRWRWKWWKK;
```

-continued

```
Peptide B2 sequence:
                                (SEQ ID NO: 2)
ILSLRWWRKWWKK;
and

Peptide B3 sequence:
                                (SEQ ID NO: 3)
ILSLRWRWWKWKK.
```

Peptide B1 contains two hydrophobic faces with one hydrophobic face interrupted by a cationic amino acid K, peptide B2 contains a single large hydrophobic face interrupted by uncharged S, and peptide B3 contains a large hydrophobic face interrupted by cationic amino acids R and K (FIG. 2). An alpha helical conformation for each peptide was predicted using PepFold and MOB software.

We also designed and tested a scrambled peptide B4, having the following sequence:

```
Peptide B4 sequence:
                                (SEQ ID NO: 4)
IRKLKSWKWLRWL.
```

The amino acids of the scrambled peptide B4 are the same as those in peptides B1, B2, and B3. However, the sequence of these amino acids in the scrambled peptide B4 was not guided by any rational design parameter.

Example 2

Peptide Synthesis and Purification

Peptides B1, B2, B3, and B4 were synthesized using an automated synthesizer (Multipep RS, Intavis Inc., Germany). Fmoc solid-phase chemistry was used to synthesize the peptides from their C-termini to N-termini on a TentaGel rink amide resin (0.25 mmol/g) (Intavis Inc.). Pre-synthesis, the resin was swollen in a DMF:DCM (2:1) solution. Post-synthesis, the resin was washed with DCM and the peptides were cleaved off using TFA/TIS/H2O (88/6/6) cocktail. Bulk TFA was removed by precipitating the peptides in ice-cold MTBE followed by centrifugation and a second MTBE wash. Peptides were air-dried and dissolved in ACN:H2O (1:5) for lyophilization. Lyophilized peptides were stored at −20.degree. C. Peptides were purified using a Waters HPLC (Waters Corporation, Milford, Mass.) with a C18 column (XBridge™ BEH130 C18 Column, Part #: 186003568, Waters Corporation). Isocratic elution was performed at 30% acetonitrile at 50.degree. C. Peptide purity increased from <50% to >90%.

Example 3

Determination of Peptide Structure by Far-Ultraviolet Circular Dichroism

Lipid films were prepared by dissolving 11.25 μmoles POPC (1-Palmitoyl-2-Oleoyl-sn-glycero-3-phosphocholine) and 3.75 μmoles POPG (1-Palmitoyl-2-Oleoyl-sn-glycero-3-phosphoglycerate) in chloroform into a round bottom flask. Chloroform was evaporated under gentle $N_2$ flow for 10 min, and lyophilized overnight to ensure complete evaporation. Lipid film was rehydrated with 3 mls 10 mM PB buffer at pH 7.4. Three freeze/thaw cycles were performed followed by a 31 pass extrusion using a 200 nm membrane at 45° C. The peptides were dissolved in 10 mM PB buffer at pH 7.4 to a concentration of 500 μM peptide. The peptides and lipids were brought to a final mole ratio of 1:10 AMP:lipid with a final concentration of 50 μM AMP. Spectra were collected using a Jasco 815 CD Spectrometer (Jasco, Easton, Md.) with a Spectrosil® Far UV Quartz cuvette (Starna Cells Inc., Atascadero, Calif., Cat #: 21-Q-1). Measurements were taken at 21° C. using 10 accumulations. Spectra were read from 260 to 190 nm with a 1.0 nm band width, a sensitivity of 100 mdeg, a response of 1 s, and a scan speed of 100 nm/min. After background subtraction, mean residual elipticity (Θ) was reported as a function of wavelength.

Results

To gain insight into the secondary structure of the designed peptides, Far-Ultraviolet Circular Dichroism ("far-UV CD") was performed with the peptides in PB buffer and in the presence of bacterial mimetic lipid vesicles (POPC:POPG 3:1 mole ratio). In PB buffer, peptides B1, B2 and B3 produced far-UV CD spectra associated with alpha-helical peptides, with Θminima at 222 nm and 205 nm in addition to an apparent maximum at 190 nm (Blondelle, Lohner, et al., Biochimica et Biophysica Acta (BBA)-Biomembranes, 1462(1):89-108 (1999); Campagna, Saint, et al., Biochemistry, 46(7):1771-1778 (2007)). The scrambled sequence B4 peptide maintained a spectrum more closely aligned with random coil/extended structure with a single minimum at 200 nm (Greenfield, Nature protocols, 1(6):2527-2535 (2006)).

In the presence of PC:PG lipid vesicles, B1 and B3 peptides retained their alpha-helical structure with characteristically similar spectra to those in PB buffer. B2 and B4 peptides had completely unique spectra when PC:PG vesicles were present. The B2 peptide spectrum contained an accentuated local maximum at 232 nm, a global minimum at 222 nm, a shoulder at 207 nm, and global max at 190 nm. Conversely, B4 peptide resulted in a slightly blue shifted spectrum yet with the same maxima but the minimum and shoulder locations swapped. These spectra contain features associated with kinked proline-rich proteins (232 nm max) and helical proteins (222 nm min, 207 nm shoulder, 190 nm max) indicating the presence of kinked helices for both B2 and B4 peptides in the presence of bacterial mimetic lipid vesicles (Greenfield, Nature protocols, 1(6): 2527-2535 (2006); Whitmore and Wallace, Biopolymers, 89(5): 392-400 2008).

Example 4

Disk Diffusion Assays

Disk diffusion assays were performed with *M. tuberculosis* mc[2] 6020 and *M. smegmatis* on 7H10 agar plates supplemented with glycerol, OADC, pantothenate and lysine as described in Sambandamurthy, et al., 2006. Vaccine, 24:6309-6320 (2006). 100 μL of a 0.25 OD600 culture (~2×106 bacteria) was spread on the surface of the agar plates prior to addition of 6 mm paper disks impregnated with 100 μg peptide dissolved in water. Control disks included water (negative) or 10 μg kanamycin (positive). Plates were incubated for three weeks at 37° C. All peptides were tested in duplicate. Antibacterial activity was visualized as clear zones around disks.

Results

Peptides B1, B2, and B3 showed inhibition against *M. tuberculosis* mc[2] 6020 and *M. smegmatis*. Kanamycin, which showed a strong signal, was used as a positive control while the negative (water) control showed no inhibition. Both peptides B1 and B3 showed better inhibition of *M. tuberculosis* mc[2] 6020 and *M. smegmatis* than peptide B2.

Example 5

Micro-Broth Dilution MIC Determinations

All antimicrobial susceptibility testing was performed in a final volume of 100 μl in sterile U-shaped 96-well polypropylene microtiter plates. Separate 96-well plates were filled with 100 μl of media broth for the growth of different test organisms. Initial AMP (B1 through B4) or gentamicin dilutions (at 512 μg/ml) were prepared and subsequent two fold dilutions were performed in 0.1 ml media broth in the microplates. Non-experimental wells were filled with sterile distilled water to prevent dehydration in experimental wells. *M. tuberculosis* (MC26230 and MC26020), *Mycobacterium smegmatis*, or BCG bacteria from frozen stocks, initially diluted to an optical density (OD) of 0.1, were each propagated at 37° C./ambient for 7 (*M. tuberculosis* mc26230, *M. smegmatis*, and BCG) to 9 days (mc26020) during which they attained a log phase growth. Following propagation, each bacterial culture was sonicated (for a total of 20 s with 5 s continuous pulses and 5 s off periods, with instrumentation settings at low power), diluted to 0.1 OD bacteria suspension, and a 1:10 dilution was further made for inoculation into the AMP-containing media broth. Five micro liter (5 μl) of the 1:10 diluted bacteria was added to each AMP-containing wells. A well without any of the AMP agent was also inoculated with 5 μl double diluted bacteria as a growth control. The plates were wrapped in aluminum foil and incubated at 37° C. for 5 days in a moisturized incubator. Following incubation, Alamar blue reagent (10 μl) was added to all experimental wells and further incubated for 24 to 48 hr. A color change from blue (inhibition) to pink (no inhibition) was observed and recorded. Visual MICs were defined as the lowest concentration of MIC that prevented a color change. For non-*M. tuberculosis* screening, fresh overnight cultures of selected gram positive bacteria (*Staphylococcus aureus* ATCC 25923, *Enterococcus faecalis* ATCC 29212, *Streptococcus pneumonia* ATCC 49619, *Streptococcus pyogens, Streptococcus agalactiae, Streptococcus mutans*, and *Bacillus subtilis*) and gram negative bacteria (*Pseudomonas aeruginosa* ATCC 27853, *Klebsiella pneumoniae* 13-329999 g, and *Escherichia coli*) were subcultured at 37° C./shaking for 3.5 to 4 hr at 200 rpm either in 5 ml Mueller-Hinton (MH; Difco) broth or MH broth supplemented with 5% sheep red blood cells. Bacteria inoculum was prepared and then added to 96-well plates containing AMPs as in *M. tuberculosis* experiments above. The plates OD before and after incubation were obtained and the difference recorded. MIC was defined as the lowest drug concentration that exhibited no growth by visual reading.

Results

In Vitro Activity and Toxicity Against *M. tuberculosis.*

The in vitro activity of the four peptides (B1, B2, B3, and B4) was measured using standard methods including a disk diffusion assay and Alimar blue assay. All three designed peptides were observed to have antimicrobial properties in the disk diffusion assay, and this activity was subsequently quantified with the Alimar blue assay. Peptide B3 was found to be active against *M. tuberculosis* MC26020 at MIC values of 8 μg/mL. Peptides B1 and B2, as well as the scrambled peptide B4, did not inhibit growth until 32 μg/mL. Considering all four peptides were derived from the same set of amino acids, this result highlights the importance of pairing database filtering with rational design. Though filtering alone resulted in a set of relatively efficacious amino acids, rational ordering of these residues improved the efficacy of peptide B3 an order of magnitude over the scrambled peptide B4.

Figure 3:
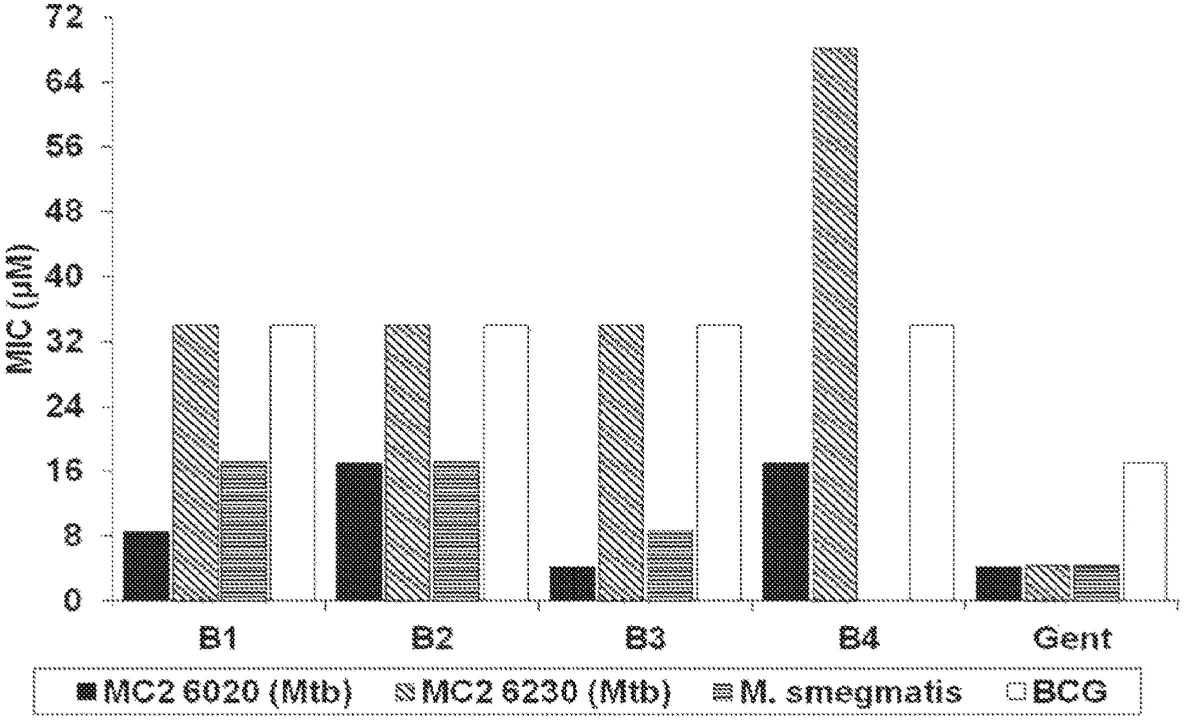
FIG. 3 illustrates minimum inhibitory concentrations ("MICs") of peptides B1 through B4 against attenuated *mycobacterium* strains. MICs were determined against two differently attenuated *M. tuberculosis* strains (MC2 6020 and MC2 6230), *M. smegmatis*, and attenuated *M. bovis* ("BCG"). On a molar basis, B3 was equally effective compared with the positive control, gentamycin ("Gent"), for *M. tuberculosis* MC2 6020. In general, the peptides were most effective against *M. tuberculosis* MC2 6020, but still remained potent against all tested *mycobacterium* strains. The MIC for B4 against *M. smegmatis* was not determined.

All four peptides were also found to be active against *M. tuberculosis* strain MC26230, but interestingly, the activity of all four peptides was attenuated. For peptide B3, the MIC was increased from 8 μg/mL to 64 μg/mL with the other peptides also showing MIC increases. Additionally the four peptides inhibited growth against other mycobacteria including *M. smegmatis* and BCG at concentrations on the same order as those for *M. tuberculosis* MC26230. The results of this study are shown in FIG. 3.

In Vitro Activity and Toxicity Against Other Clinically Relevant Bacteria

In addition to tuberculosis, the four peptides were tested against several strains of clinically relevant gram-positive and gram-negative bacteria. In general, the peptides were more potent against gram-positive species than gram-negative species. The peptides were especially potent against *streptococcus* species, with MIC values as low as 4 μg/mL. The peptides were less efficacious against some microbes such as *E. faecalis* with MICs of 512 μg/mL. While consistent with previous findings that cationic, amphipathic peptides are broadly active, the range of potencies highlights the need for species specific database optimization during peptide design.

Figure 4:
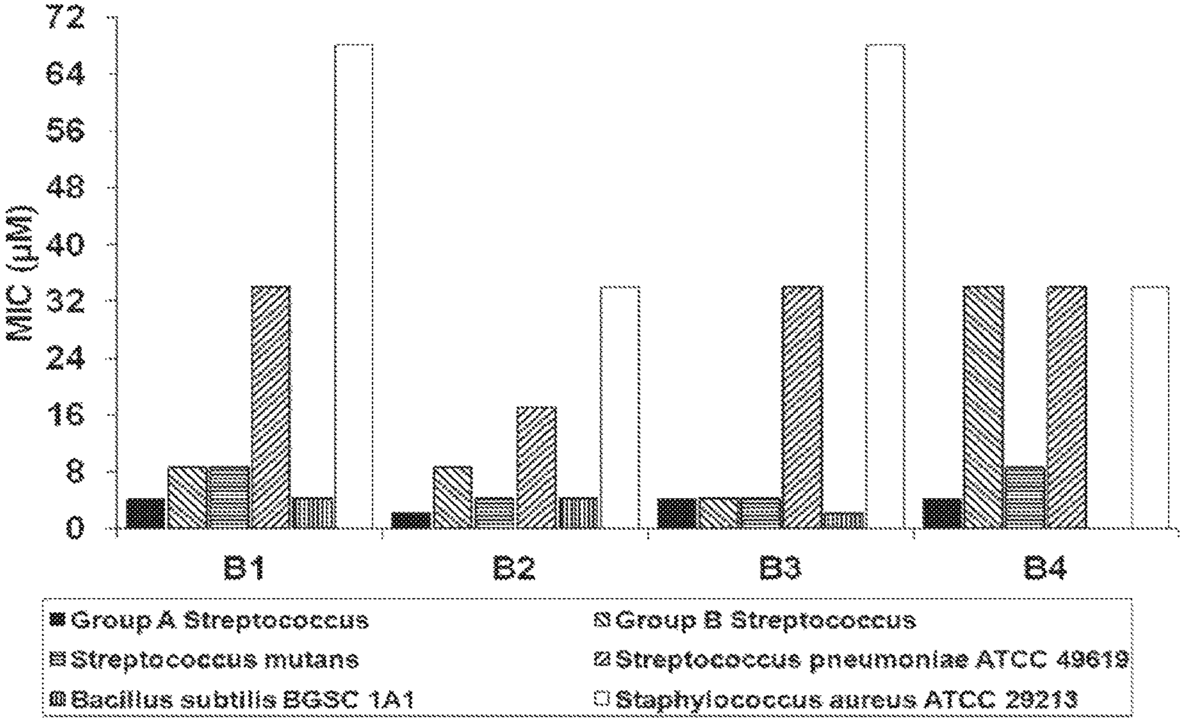
FIG. 4 illustrates MICs of peptides B1 through B4 against clinically relevant Gram-positive bacteria. MICs were determined against the six Gram-positive bacteria given in the legend. The designed peptides proved very effective against *B. subtilis* and various strains of *streptococcus*. The MIC for B4 against *B. subtilis* was not determined.
Figure 5:
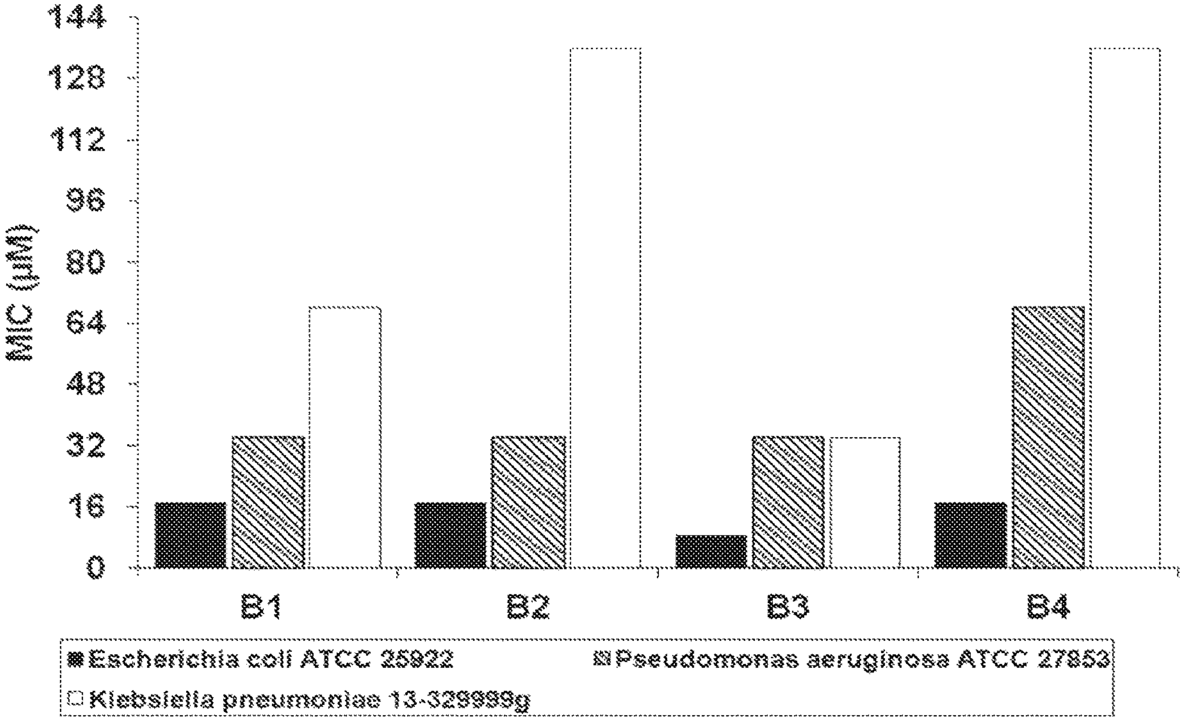
FIG. 5 illustrates MICs of peptides B1 through B4 against clinically relevant Gram-negative bacteria. MICs were determined against the three Gram-negative bacteria given in the legend. Out of the Gram-negative bacteria, the designed peptides proved most effective against *E. coli*. The designed peptides successfully inhibited the growth of all Gram-negative bacteria tested.

Interestingly, in most cases against gram-negative bacteria peptide B2 was more potent than B3. This was not observed with *M. tuberculosis*. This result again illustrates the importance of amino acid ordering and indicates that the mechanism of antimicrobial activity may differ between gram-positive bacteria and tuberculosis, which is neither gram-positive nor-negative. The results of this study are shown in FIGS. 4 and 5.

Example 6

Assay for Peptide Cytotoxicity Against Mammalian Cells

Figure 6:
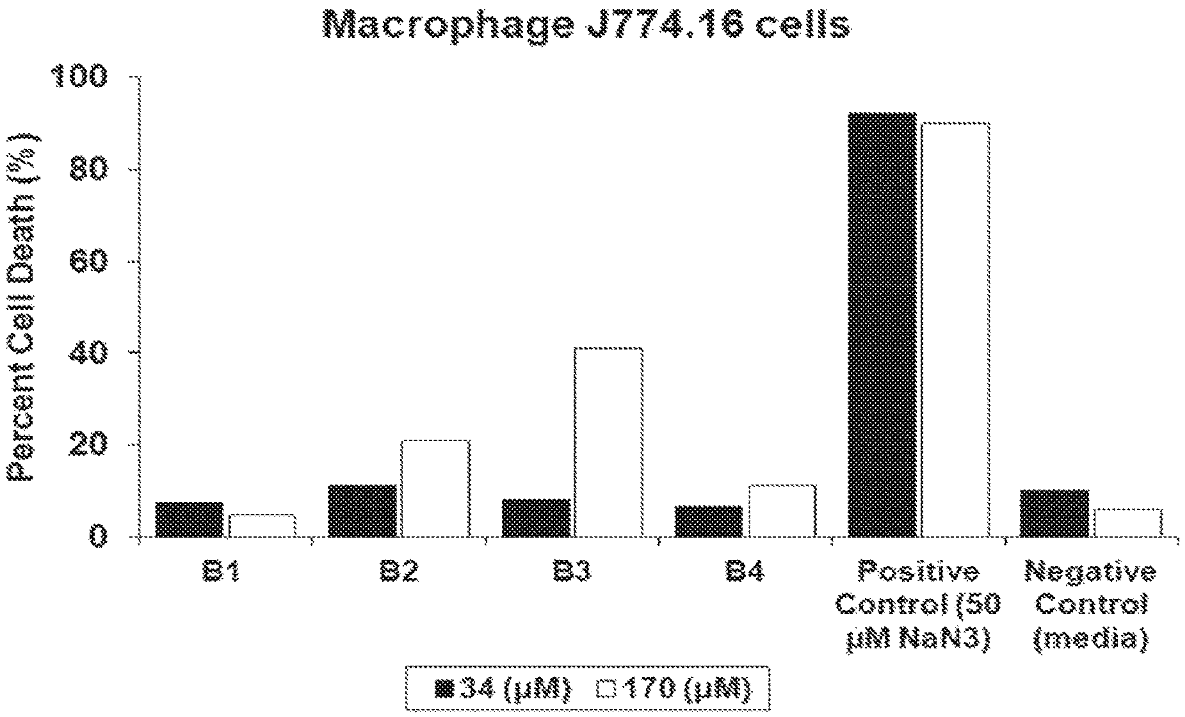
FIG. 6 illustrates cytotoxicity of peptides B1 through B4 against Mammalian Macrophage J774.16 Cells. There was no observable cytotoxicity at 34 μM peptide concentration. 20% cell death was observed for peptide B2 at 170 μM, while 40% cell death resulted from peptide B3 incubation at 170 μM, both toxic above the value of the negative control (10%). Still, the peptides have minimal cytotoxicity against macrophage J774.16 cells even at higher concentrations.
Figure 7:
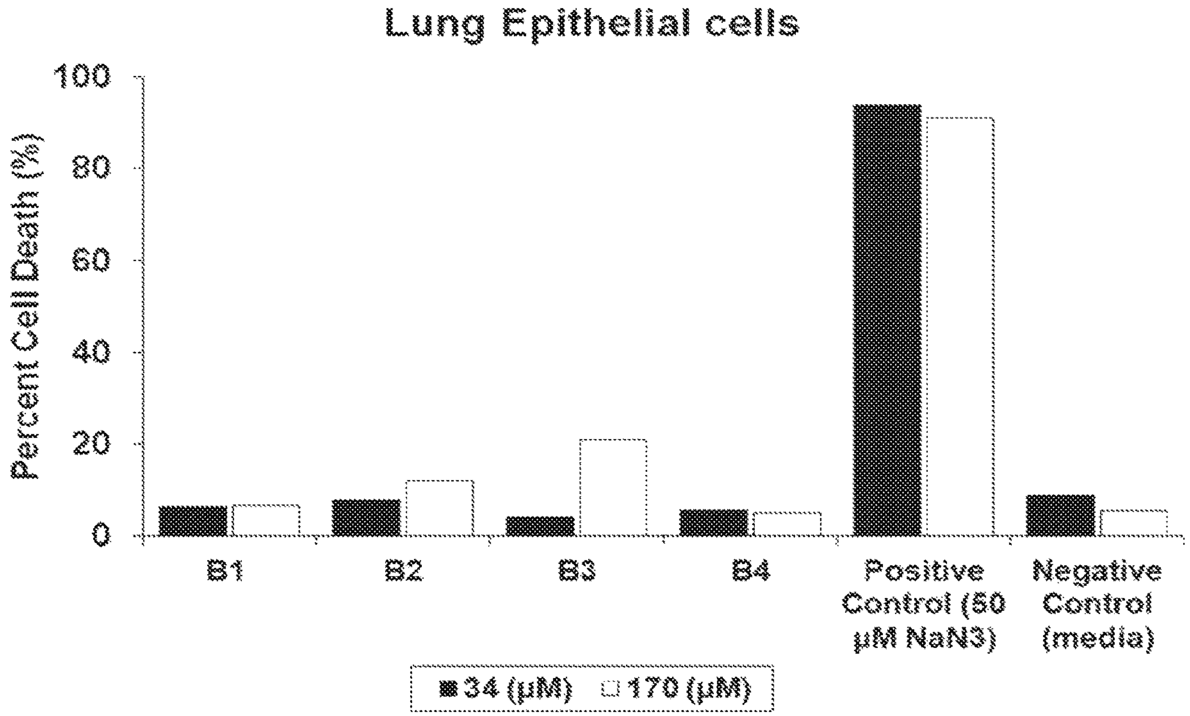
FIG. 7 illustrates cytotoxicity of peptides B1 through B4 against Mammalian Lung Epithelial Cells. There was no observable cytotoxicity at 34 μM peptide concentration. Slight cytotoxicity was seen for peptides B2 and B3 at 170 μM peptide concentration compared with the negative control.

Cytotoxicity studies were performed using three mammalian cell lines which included mouse macrophage J774.16 cell line, human lung epithelial A549 cell line, and sheep red blood cells (sRBCs) in Trypticase soy agar (TSA). Mouse macrophage J774.16 cell line (maintained in antibiotic-free Dulbecco's modified Eagle's medium containing 20% fetal bovine serum, 5% NCTC 109, 1% nonessential amino acids and 1% glutamine) or human lung epithelial A549 cell line (maintained in antibiotic-free Ham's F12 medium supplemented with 10% fetal bovine serum) was seeded at a density of approximately 1.times.105 cells per ml in Lab-tek Permanox eight-chamber microscopy slides (Nunc, Inc., Naperville, Ill.) and incubated for 3 (J774.16) or 5 (A549) days before use. After cell differentiation to a confluence of 70 to 80%, the culture media was replaced with fresh media containing the different AMPS at 64 μg/ml or at toxic dose (320 μg/ml) or controls (media only for negative control or 50 μM NaN3 for positive control). Similarly, AMPS or 1% Triton 100-X as positive control or media only (negative control) was each added to separate wells and allowed to be absorbed into agar at room temperature. All experiments were incubated for 24 hr at 37° C., 5% CO2. All experiments were done in duplicates. Cytotoxicity for J774.16 or A549 cells was monitored using Trypan Blue exclusion assay and the ratio of dead to viable cells was recorded. For sRBCs, the presence of cell lysis after 24 hr of incubation at 37.degree. C. following treatment indicated cytotoxicity. The results of this study are shown in FIG. 6.

Results

Cytotoxicity Against Mammalian Cells

To check for cytotoxicity against mammalian cells, the four peptides were tested against macrophage J774.16 cells, lung epithelial cells, and sheep red blood cells. All peptides tested were non-toxic to mammalian cells at the MICs required for antimicrobial activity. Peptide B3, the most potent antimicrobial peptide, began to show moderate cytotoxicity against macrophage J774.16 cells at 320 m/mL, which is at least five times the MIC of this peptide against mycobacteria and streptococci. B3 similarly exhibited some degree of cytotoxicity in lung epithelial cells, however, the cytotoxicity level was relatively milder when compared to that on J774.16 cells. The results of this study are shown in FIG. 6.

The lack of cytotoxicity of our novel peptides is likely due to the designed inclusion of at least one cationic residue within the hydrophobic face, following the imperfect amphipathicity approach of Wimley (Wimley and Hristova, Journal of Membrane Biology, 239(1-2):27-34 (2011)). This lack of cytotoxicity is important because to be useful as a broad-spectrum anti-microbial drug, it is necessary to dissociate anti-eukaryotic activity from antimicrobial activity, i.e., increasing the antimicrobial activity and reducing toxicity to normal cells.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 1

Ile Leu Ser Leu Arg Trp Arg Trp Lys Trp Trp Lys Lys
1               5                   10


<210> SEQ ID NO 2
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 2

Ile Leu Ser Leu Arg Trp Trp Arg Lys Trp Trp Lys Lys
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 3

Ile Leu Ser Leu Arg Trp Arg Trp Trp Lys Trp Lys Lys
1               5                   10


<210> SEQ ID NO 4
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 4

Ile Arg Lys Leu Lys Ser Trp Lys Trp Leu Arg Trp Leu
1               5                   10


<210> SEQ ID NO 5
<211> LENGTH: 13
```

-continued

<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (7)..(8)
<223> OTHER INFORMATION: Xaa7 and Xaa8 are selected from the group
      consisting of R and W, wherein X7 and X8 are not the same
<220> FEATURE:
<221> NAME/KEY: MISC_FEATURE
<222> LOCATION: (9)..(10)
<223> OTHER INFORMATION: Xaa9 and Xaa10 are selected from the group
      consisting of K and W, wherein Xaa9 and Xaa10 are not the same

<400> SEQUENCE: 5

Ile Leu Ser Leu Arg Trp Xaa Xaa Xaa Xaa Trp Lys Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (1)..(2)
<223> OTHER INFORMATION: Xaa1 and Xaa2 are each a hydrophobic amino acid
<220> FEATURE:
<221> NAME/KEY: MISC_FEATURE
<222> LOCATION: (3)..(3)
<223> OTHER INFORMATION: Xaa3 is selected from the group consisting of
      S, T, N, and Q
<220> FEATURE:
<221> NAME/KEY: MISC_FEATURE
<222> LOCATION: (4)..(4)
<223> OTHER INFORMATION: Xaa4 is a hydrophobic amino acid
<220> FEATURE:
<221> NAME/KEY: MISC_FEATURE
<222> LOCATION: (5)..(5)
<223> OTHER INFORMATION: Xaa5 is a cationic amino acid
<220> FEATURE:
<221> NAME/KEY: MISC_FEATURE
<222> LOCATION: (6)..(6)
<223> OTHER INFORMATION: Xaa6 is a hydrophobic amino acid
<220> FEATURE:
<221> NAME/KEY: MISC_FEATURE
<222> LOCATION: (7)..(8)
<223> OTHER INFORMATION: Xaa7 and Xaa8 are selected from the group
      consisting of a hydrophobic amino acid and a cationic amino acid,
      wherein Xaa7 and Xaa8 cannot both be a hydrophobic amino acid and
      cannot both be a cationic amino acid
<220> FEATURE:
<221> NAME/KEY: MISC_FEATURE
<222> LOCATION: (9)..(10)
<223> OTHER INFORMATION: Xaa9 and Xaa10 are selected from the group
      consisting of a hydrophobic amino acid and a cationic amino acid,
      wherein Xaa9 and Xaa10 cannot both be a hydrophobic amino acid and
      cannot both be a cationic amino acid
<220> FEATURE:
<221> NAME/KEY: MISC_FEATURE
<222> LOCATION: (11)..(11)
<223> OTHER INFORMATION: Xaa11 is a hydrophobic amino acid
<220> FEATURE:
<221> NAME/KEY: MISC_FEATURE
<222> LOCATION: (12)..(13)
<223> OTHER INFORMATION: Xaa12 and Xaa13 are each a cationic amino acid

<400> SEQUENCE: 6

Xaa Xaa Xaa Xaa Xaa Xaa Xaa Xaa Xaa Xaa Xaa Xaa Xaa
1               5                   10

What is claimed is:

1. An isolated peptide comprising a sequence $X_1X_2X_3X_4X_5X_6X_7X_8X_9X_{10}X_{11}X_{12}X_{13}$ (SEQ ID NO: 6), wherein:

$X_1$, $X_2$, $X_4$, $X_6$, and $X_{11}$ are selected from the group consisting of I, L, and W, $X_3$ is selected from the group consisting of S or T, $X_5$, $X_{12}$, and $X_{13}$ are selected from the group consisting of K and R, $X_7$ and $X_8$ are selected from the group consisting of R and W, wherein $X_7$ and $X_8$ are not the same, $X_9$ and $X_{10}$ are selected from the group consisting of K and W, wherein $X_9$ and $X_{10}$ are not the same.

2. The peptide according to claim 1, wherein $X_3$ is S.

3. The peptide according to claim 1, wherein the peptide includes at least one D-amino acid.

4. The peptide according to claim 1, wherein the peptide includes at least one modification includes amidation, acetylation, halogenation, or combinations thereof.

5. A composition including at least one peptide of claim 1 and a pharmaceutically acceptable buffer, diluent, carrier, adjuvant, or excipient.

6. The composition according to claim 5, further comprising at least one antibiotic agent.

7. The composition according to claim 6, wherein the at least one antibiotic agent is selected from the group consisting of isoniazid, rifampicin, pyrazinamide, ethambutol, levofloxacin, moxifloxacin, ofloxacin, kanamycin, amikacin, capreomycin, streptomycin, bedaquiline, para-aminosalicyclic acid, para-aminoslicyclic acid, cycloserine, and combinations thereof.

8. A disinfecting solution includes the peptide of claim 1 and an acceptable carrier.

9. The peptide according to claim 1, wherein the peptide includes IRKLKSWKWLRWL (SEQ ID NO: 4).

10. The peptide according to claim 9, wherein the peptide includes at least one D-amino acid.

11. A composition including at least one peptide of claim 9, and a pharmaceutically acceptable buffer, diluent, carrier, adjuvant, or excipient.

12. The composition according to claim 11, further comprising at least one antibiotic agent, wherein the at least one antibiotic agent is selected from the group consisting of isoniazid, rifampicin, pyrazinamide, ethambutol, levofloxacin, moxifloxacin, ofloxacin, kanamycin, amikacin, capreomycin, streptomycin, bedaquiline, para-aminosalicyclic acid, para-aminoslicyclic acid, cycloserine, and combinations thereof.

13. The peptide according to claim 9, wherein the peptide includes at least one modification includes amidation, acetylation, halogenation, or combinations thereof.

14. A disinfecting solution includes the peptide of claim 9 and an acceptable carrier.

* * * * *